US010219708B2

(12) United States Patent
Altini

(10) Patent No.: US 10,219,708 B2
(45) Date of Patent: Mar. 5, 2019

(54) DEVICE AND METHOD FOR CALCULATING CARDIORESPIRATORY FITNESS LEVEL AND ENERGY EXPENDITURE OF A LIVING BEING

(71) Applicant: Stichting IMEC Nederland, Eindhoven (NL)

(72) Inventor: Marco Altini, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 25 days.

(21) Appl. No.: 14/133,490

(22) Filed: Dec. 18, 2013

(65) Prior Publication Data

US 2014/0180033 A1 Jun. 26, 2014

(30) Foreign Application Priority Data

Dec. 19, 2012 (EP) .................................... 12198099

(51) Int. Cl.

*A61B 5/024* (2006.01)
*A61B 5/11* (2006.01)
*A61B 5/22* (2006.01)

(52) U.S. Cl.

CPC ........ *A61B 5/02405* (2013.01); *A61B 5/1118* (2013.01); *A61B 5/1123* (2013.01); *A61B 5/222* (2013.01); *F04C 2270/041* (2013.01)

(58) Field of Classification Search

CPC ..... A61B 5/222; A61B 5/1123; A61B 5/0255; A61B 5/02405; A61B 5/1118; A61B 5/11
See application file for complete search history.

(56) References Cited

U.S. PATENT DOCUMENTS 5,263,491 A * 11/1993 Thornton ................. A61B 5/22 600/483
5,976,083 A * 11/1999 Richardson .......... A61B 5/0245 482/8

(Continued)

FOREIGN PATENT DOCUMENTS

WO WO 2005/011480 2/2005
WO WO 2012/140322 10/2012

OTHER PUBLICATIONS

E. Tapia, "Using Machine Learning for Real-time Activity Recognition and Estimation of Energy Expenditure", Ph.D, Massachusetts Institute of Technology, 2008.*

(Continued)

*Primary Examiner* — Christopher D Koharski
*Assistant Examiner* — Amanda Steinberg
(74) *Attorney, Agent, or Firm* — Knobbe Martens Olson & Bear LLP

(57) ABSTRACT

A device for monitoring the physical activity of a living being is disclosed. In one aspect, there is a data input module configured to receive information about the living being's heart beat rate value, motion intensity and anthropometric characteristics. Further, there is an activity recognition and storage module configured to detect, from information received about the living being's motion intensity, the living being's activity and to store information about the living being's heart beat rate value and the motion intensity associated with that detected activity. Further, there is a heart beat rate analysis module configured to determine, from a plurality of heart beat rate values associated with each detected activity, statistics of the distribution of heart beat rate values for each activity or a subset of activities. Further, there is a fitness estimation module configured to calculate, using the information from the heart beat rate analysis (Continued)

module and the anthropometric characteristics, a cardio-respiratory fitness level of the living being.

15 Claims, 8 Drawing Sheets

(56) References Cited

U.S. PATENT DOCUMENTS

| | | | | |
|---|---|---|---|---|
| 6,030,342 | A * | 2/2000 | Amano | A61B 5/02055 600/301 |
| 6,042,549 | A * | 3/2000 | Amano | A61B 5/02438 600/500 |
| 6,571,200 | B1 * | 5/2003 | Mault | A61B 5/0002 702/131 |
| 7,676,332 | B2 * | 3/2010 | Damen | A61B 5/222 600/300 |
| 8,398,546 | B2 * | 3/2013 | Pacione | A61B 5/411 128/920 |
| 9,081,534 | B2 * | 7/2015 | Yuen | G06F 11/00 |
| 2003/0226695 | A1 * | 12/2003 | Mault | A61B 5/0002 177/25.16 |
| 2005/0033200 | A1 * | 2/2005 | Soehren | A61B 5/0002 600/595 |
| 2005/0119833 | A1 * | 6/2005 | Nanikashvili | A61B 5/02438 702/19 |
| 2005/0148827 | A1 * | 7/2005 | Chen | A61B 5/02438 600/300 |
| 2006/0020177 | A1 * | 1/2006 | Seo | A61B 5/222 600/300 |
| 2007/0219059 | A1 * | 9/2007 | Schwartz | A61B 5/0205 482/8 |
| 2008/0009393 | A1 * | 1/2008 | Glusco | A61B 5/0205 482/8 |
| 2009/0082681 | A1 * | 3/2009 | Yokoyama | A61B 5/024 600/509 |
| 2009/0171614 | A1 * | 7/2009 | Damen | A61B 5/222 702/141 |
| 2011/0021319 | A1 * | 1/2011 | Nissila | A61B 5/222 482/8 |
| 2011/0275940 | A1 * | 11/2011 | Nims | A61B 5/222 600/483 |
| 2012/0083705 | A1 * | 4/2012 | Yuen | A61B 5/0002 600/508 |
| 2012/0215116 | A1 * | 8/2012 | Martikka | A61B 5/0205 600/484 |
| 2012/0232413 | A1 * | 9/2012 | Shiota | A61B 5/02411 600/500 |
| 2013/0173174 | A1 * | 7/2013 | Baxi | A61B 5/6898 702/19 |

OTHER PUBLICATIONS

Altini et al., "Energy Expenditure Estimation Using Wearable Sensors: A New Methodology for Activity-Specific Models," Wireless Health '12; 8 pages; San Diego, USA; (Oct. 2012).

Brage et al., "Branched equation modeling of simultaneous accelerometry and heart rate monitoring improves estimate of directly measured physical activity energy expenditure," J Appl Physiol; 96:343-351; (2003).

Brage et al., "Hierarchy of individual calibration levels for heart rate and accelerometry to measure physical activity," J Appl Physiol; 103:682-692; (2007).

Butte et al., "Validation of Cross-Sectional Time Series and Multivariate Adaptive Regression Splines Models for the Prediction of Energy Expenditure in Children and Adolescents Using Doubly Labeled Water," The Journal of Nutrition; 140(8): 1516-1523; (2010).

Esco et al, "Cross-Validation of the Polar Fitness Test™ via the Polar F11 Heart Rate Monitor in Predicting $VO_2$ Max," Journal of Exercise Physiologyonline; vol. 14, No. 5; pp. 31-37; (2011).

Plasqui et al., "Accelerometry and Heart Rate as a Measure of Physical Fitness: Proof of Concept," Medicine and Science in Sports and Exercise; pp. 872-876; (2005).

Rumo et al., "A stepwise validation of a wearable system for estimating energy expenditure in field-based research," Physiol. Meas.; vol. 32, No. 12; 1983-2001; (2011).

Tapia et al., "Real-Time Recognition of Physical Activities and Their Intensities Using Wireless Accelerometers and a Heart Rate Monitor," 11$^{th}$ IEEE International Symposium on Wearable Computers; 37-40; (2007).

Tapia, "Using Machine Learning for Real-time Activity Recognition and Estimation of Energy Expenditure," Excerpt of Doctoral Dissertation, Massachusetts Institute of Technology; pp. 3, 134-144, 205-210, 238-245; (2008).

Tonis et al., "Using combined accelerometer and heart rate data to estimate physical fitness," Roessingh Research & Development, accessed at http://www.rrd.nl/docs/posters/Tonis%20T%20-%20Using%20Combined.pdf on Mar. 7, 2014.

Extended European Search Report dated Jun. 5, 2013 for European Patent Application No. 12198099.9 related to U.S. Appl. No. 14/133,490.

* cited by examiner

DEVICE AND METHOD FOR CALCULATING CARDIORESPIRATORY FITNESS LEVEL AND ENERGY EXPENDITURE OF A LIVING BEING

CROSS REFERENCE TO RELATED APPLICATIONS

This application claims priority under 35 U.S.C. § 119 (a)-(d) to European Patent Application No. EP 12198099.9, filed Dec. 19, 2012, the disclosure of which is hereby incorporated by reference in its entirety.

BACKGROUND

Technological Field

The present disclosure is related to devices and methods for monitoring physical activity of living beings and more specifically for calculating the cardiorespiratory fitness level and energy expenditure of a living being.

Description of the Related Technology

Current technologies for estimating energy expenditure (EE) and cardiorespiratory fitness (CRF) can provide useful insights about a living being's physical activity and health.

CRF can be estimated using maximal tests, but such tests require medical supervision and cannot be performed by everyone. There are also known methods, such as the one described in "*Cross-Validation of the Polar Fitness Test via the Polar F*11 *Heart Rate Monitor in Predicting VO2Ma*," by Michael R. Esco, Emmanuel M. Mugu, Henry N. Williford, Aindrea N. McHugh and Barbara E. Bloomquist, in Journal of Exercise Physiology, 2011, which calculate CRF using sub-maximal tests. However, such techniques require both a specific test and repeating such specific test every time the CRF needs to be assessed.

In a similar way, current EE estimation techniques present also some limitations, for example, either provide inaccurate EE values, such as in "*Branched equation modeling of simultaneous accelerometry and heart rate monitoring improves estimate of directly measured physical activity energy expenditure*," by S. Brage, in Journal of Applied Physiology, 96(1):343-351, Aug. 2003; or perform individual calibration using an indirect calorimeter, such as in "*Hierarchy of individual calibration levels for heart rate and accelerometry to measure physical activity*," by S. Brage, U. Ekelund, N. Brage, M. A. Hennings, K. Froberg, P. W. Franks, and N. J. Wareham, in Journal of Applied Physiology, 2007, which requires a specific test with a very costly device.

Therefore, there is a need for ambulatory and/or more accurate and cheap automatic solutions for calculating cardiorespiratory fitness levels and energy expenditures of living beings, such as humans or animals, which may use wearable sensors and can be comfortably carried during activities of daily living.

SUMMARY OF CERTAIN INVENTIVE ASPECTS

According to one embodiment, there is provided a device for monitoring the physical activity of a living being comprising: a data input module configured to receive information about the living being's heart beat rate value, motion intensity and anthropometric characteristics; an activity recognition and storage module configured to detect, from information received about the living being's motion intensity, the living being's activity and to store information about said living being's heart beat rate value and said motion intensity associated with that detected activity; a heart beat rate analysis module configured to determine, from a plurality of heart beat rate values associated with each detected activity, statistics of the distribution of heart beat rate values for each activity or a subset of activities; and a fitness estimation module configured to calculate, using the information from the heart beat rate analysis module and the anthropometric characteristics, a cardiorespiratory fitness level of the living being.

Advantageously, according to one embodiment, the device is able to calculate a cardiorespiratory fitness level of a living being, such as a human or animal, without the need to perform a specific exercise test. Additionally, the device according to one embodiment is able to continuously and automatically recalculate the cardiorespiratory fitness level of the living being over time, by gathering data about the living being's activities and heart beat rate values, so that the cardiorespiratory fitness level is updated, avoiding the need to perform further exercise tests. This is advantageous since the device according to one embodiment is able to monitor the cardiorespiratory fitness level during the lifetime of a living being in a non-invasively manner and seamlessly integrated without affecting the daily normal activities of the living being. According to one embodiment, the device performs activity recognition from the received living being's motion intensity information and associates those activities to the heart beat rate values of the subject when performing those activities. Advantageously said activities are different activities of daily living. Then, the device according to one embodiment uses the heart beat rate information from the living being at different workloads and calculates the cardiorespiratory fitness level.

According to another embodiment, the information about motion intensity may be information about the body's acceleration and/or motion speed. According to another embodiment, the information about motion intensity may be information about the body's acceleration and the device further comprises motion calculation means configured to calculate, from said information about the body's acceleration, the living being's motion speed. According to another embodiment, the information about motion intensity may be information about the body's acceleration and the device further comprises location positioning means configured to calculate the living being's motion speed.

According to still another embodiment, the heart beat rate analysis module is configured to calculate statistics of the heart beat rate value distribution associated to a detected activity and motion intensity in order to store summarized heart beat rate information for each activity or a subset of activities. For example, the heart beat rate analysis module may calculate the mean or the median of the heart beat rate value distribution associated to a detected activity and motion intensity, so that from a plurality of heart beat rate values associated to a detected activity and motion intensity, the heart beat rate analysis module summarizes that plurality of values in one or more heart beat rate values.

According to another embodiment, the fitness estimation module may use a mathematical model based on information about heart beat rate value distribution, acceleration, anthropometric characteristics and VO2 reference from indirect calorimetry. Examples of such mathematical model may be multiple linear regression models. The coefficients of the multiple linear regression models may be derived using information about activity performed, heart beat rate distribution, acceleration, anthropometric characteristics and VO2 reference from indirect calorimetry from a number of living beings, e.g. humans, performing a range of different activities.

According to still another embodiment, the mathematical model expresses the relation between the summarized heart beat rate values, the associated detected activity or subset of activities, the associated motion intensity, the anthropometric characteristics and the cardiorespiratory fitness level of the living being.

According to still another embodiment, the device further comprises an energy expenditure module configured to calculate an energy expenditure of a living being using information about the living being's cardiorespiratory fitness level, detected activity, motion intensity, normalized heart beat rate values and the anthropometric characteristics.

Advantageously, the device for monitoring the physical activity of a living being according to one embodiment, further uses the information about the living being's cardiorespiratory fitness level to calculate the energy expenditure, and thereby improving the accuracy of the energy expenditure values provided for that living being. The device according to one embodiment advantageously improves the accuracy of heart beat rate based EE estimation over time by using the cardiorespiratory fitness level to normalize the heart beat rate information of the living being during activities of daily living.

According to one embodiment, the activity recognition and storage module may be configured to detect both a rest activity and a moving activity, and to store heart beat rate values associated with each detected activity, and furthermore, the motion intensity associated to the moving activity.

According to still another embodiment, the moving activity may be associated to at least a first motion intensity and a second motion intensity and the heart beat rate analysis module determines one first heart beat rate summary from the heart beat rate value distribution associated to the first motion intensity and one second heart beat rate summary from the heart beat rate value distribution associated to the second motion intensity and one third heart beat rate summary from the heart beat rate value distribution associated to the rest activity.

The description also relates to a method for monitoring the physical activity of living beings, the method comprising:

receiving information about the living being's heart beat rate value, motion intensity and anthropometric characteristics; detecting the living being's activity from information received about the living being's motion intensity and storing information about said living being's heart beat rate value and said motion intensity associated with that detected activity; determining, from a plurality of heart beat rate values associated with each detected activity, statistics of the distribution of heart beat rate values for each activity or a subset of activities; and calculating, using the information from the heart beat rate analysis module and the anthropometric characteristics, a cardiorespiratory fitness level of the living being.

According to another embodiment, the method further calculates, using the information from the living being's cardiorespiratory fitness level, detected activity, motion intensity, normalized heart beat rate values and the anthropometric characteristics, an energy expenditure of the living being.

The description also relates to a system for monitoring physical activity of living beings comprising a device for calculating the cardiorespiratory fitness level or energy expenditure of a living being according to any of the embodiments herein described.

BRIEF DESCRIPTION OF THE DRAWINGS

The above summary and other aspects will be apparent from the following description and with reference to the non-restrictive example embodiments described hereinafter.

DETAILED DESCRIPTION OF CERTAIN ILLUSTRATIVE EMBODIMENTS

Figure 1:
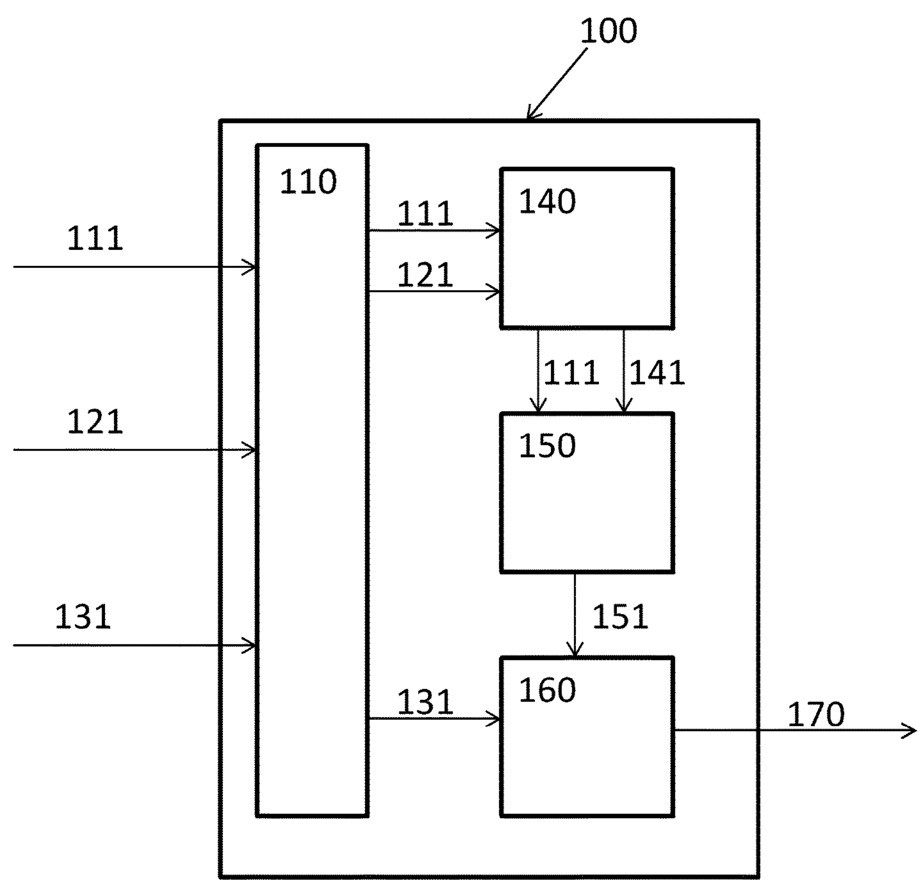
FIG. 1 shows a block diagram of a first embodiment of a device for monitoring the physical activity of a living being.

FIG. 1 shows a first block diagram of one embodiment of a device 100 for monitoring the physical activity of a living being comprising a data input module 110 which receives information about the living being's heart beat rate value 111, motion intensity 121 and anthropometric characteristics 131; an activity recognition and storage module 140, which determines, from information received about the living being's motion intensity 121, the living being's different activities 141 and stores information about the living being's heart beat rate value 111 and motion intensity 121 associated with each of the detected activities 141; a heart beat rate analysis module 150, which determines, from a plurality of heart beat rate values 111 associated with each detected activity 141, statistics of the distribution of heart beat values 151 for each activity or a subset of activities; and a fitness estimation module 160, which calculates, using the information from the heart beat rate analysis module 150 and the anthropometric characteristics 131, a cardiorespiratory fitness level 170 of the living being.

Information about the living being's heart beat rate 111 can be received from a heart beat rate or ECG sensor, and may be information about current or real-time heart rate of the subject.

According to one embodiment, the information about motion intensity 121 may be information about the living being body's acceleration and/or motion speed. This information may be provided, for example by an accelerometer sensor and/or by a GPS device connected or sending information to the device 100. According to another embodiment, the information about motion intensity 121 may be information about the body's acceleration and the device 100 further comprises motion calculation means which calculate, from said information about the body's acceleration, the living being's motion speed. Motion calculation means can include, but is not limited to, a computer, a microprocessor, or a microcontroller that includes motion calculation algorithms. According to another embodiment, the information about motion intensity 121 may be information about the body's acceleration and the device 100 further comprises location positioning means, such as a GPS device, which calculate the living being's motion speed.

According to another embodiment, information about the anthropometric characteristics 131 of the living being can be information received from an input user interface in which any information about, for example and when applicable, the type, gender, BMI, height, age, weight of the living being can be provided to the system.

It is also understood that the device 100 can receive all information needed for its functions from sensors or interface units directly connected to the device or via a wireless transmission module which receives information from sensors located in different locations of the living being. Therefore, the device 100 may be attached to the living being's body or separated from it, for example, implemented in a separate mobile unit or integrated in a mobile phone.

Figure 3A:
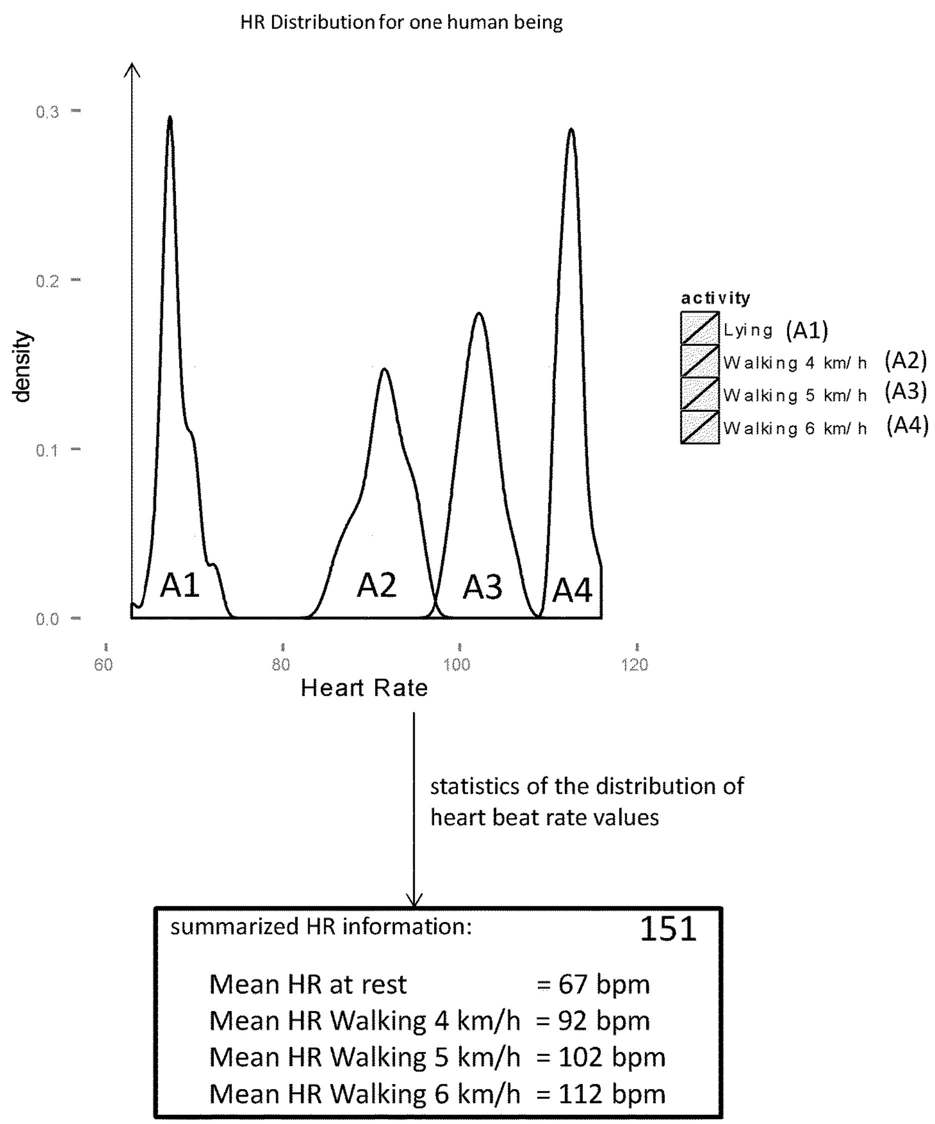
FIG. 3A illustrates the distribution of a plurality of heart beat rate values associated with four detected activities, used for calculating statistics of the distribution of heart beat values according to one embodiment.

According to a further embodiment, the heart beat rate analysis module 150 calculates statistics of the heart beat rate value distribution associated to a detected activity 141 and motion intensity 121 in order to store summarized heart rate information 151 for each activity or a subset of activities. For example, according to one embodiment, as shown in FIG. 3A, the mean heart beat rate values while resting (the activity recognition and storage module 140 detecting the activity "lying down") and walking at 4, 5 and 6 km/h (the activity recognition and storage module 140 detecting the activity "walking," together with "walking speed") could be stored. Alternatively another calculation of statistics of the heart beat rate value distribution associated to a detected activity that could be used for summarizing heart rate information is by calculating the median of the heart beat rate values associated to each activity. Storing of information can be done on an internal or external memory to the device 100.

Figure 3B:
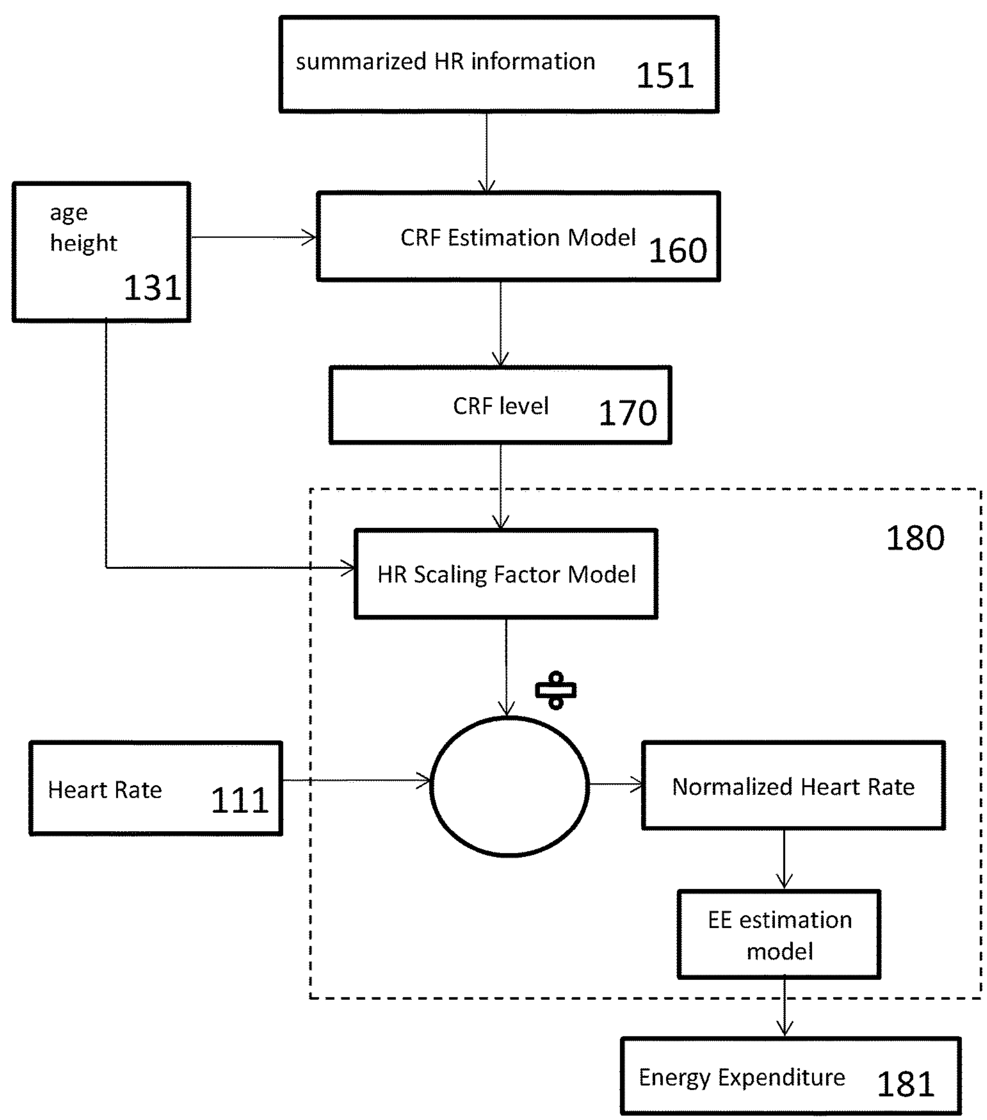
FIG. 3B shows a flow diagram illustrating how summarized heart beat rate information may be used, together with anthropometric characteristics and heart beat rate for calculating a CRF level and EE according to one embodiment.

According to still another embodiment, the fitness estimation module 160 uses a mathematical model based on information about heart beat rate distribution, acceleration, anthropometric characteristics and VO2 reference from indirect calorimetry. For example, according to one embodiment the mean (or median) heart rate while resting and walking at 4, 5 and 6 km/h can be used together with age and height to predict cardiorespiratory fitness level using a multiple linear regression model. A similar mathematical model based on information about heart beat rate distribution, acceleration and anthropometric characteristics (but not necessarily information about VO2) can be used to derive a heart rate scaling factor, which is a heart rate value representative of the cardiorespiratory fitness level of the human being. Alternatively, according to another embodiment, as shown in FIG. 3B, the heart rate scaling factor can be derived by the cardiorespiratory fitness level directly, for example by means of another linear (or non-linear) model.

According to another embodiment, the mathematical model expresses the relation between the summary of heart rate values one heart beat rate value 151, the associated detected activity or subset of activities 141, the associated motion intensity 121, the anthropometric characteristics 131 and the cardiorespiratory fitness level 170 of the living being. For example, according to one embodiment, as shown in FIG. 3B, the heart rate scaling factor value, representative of the cardiorespiratory fitness level of the human being, can be used to derive a normalized heart rate, for example by dividing the current heart rate of the subject by the heart rate scaling factor.

Figure 4A:
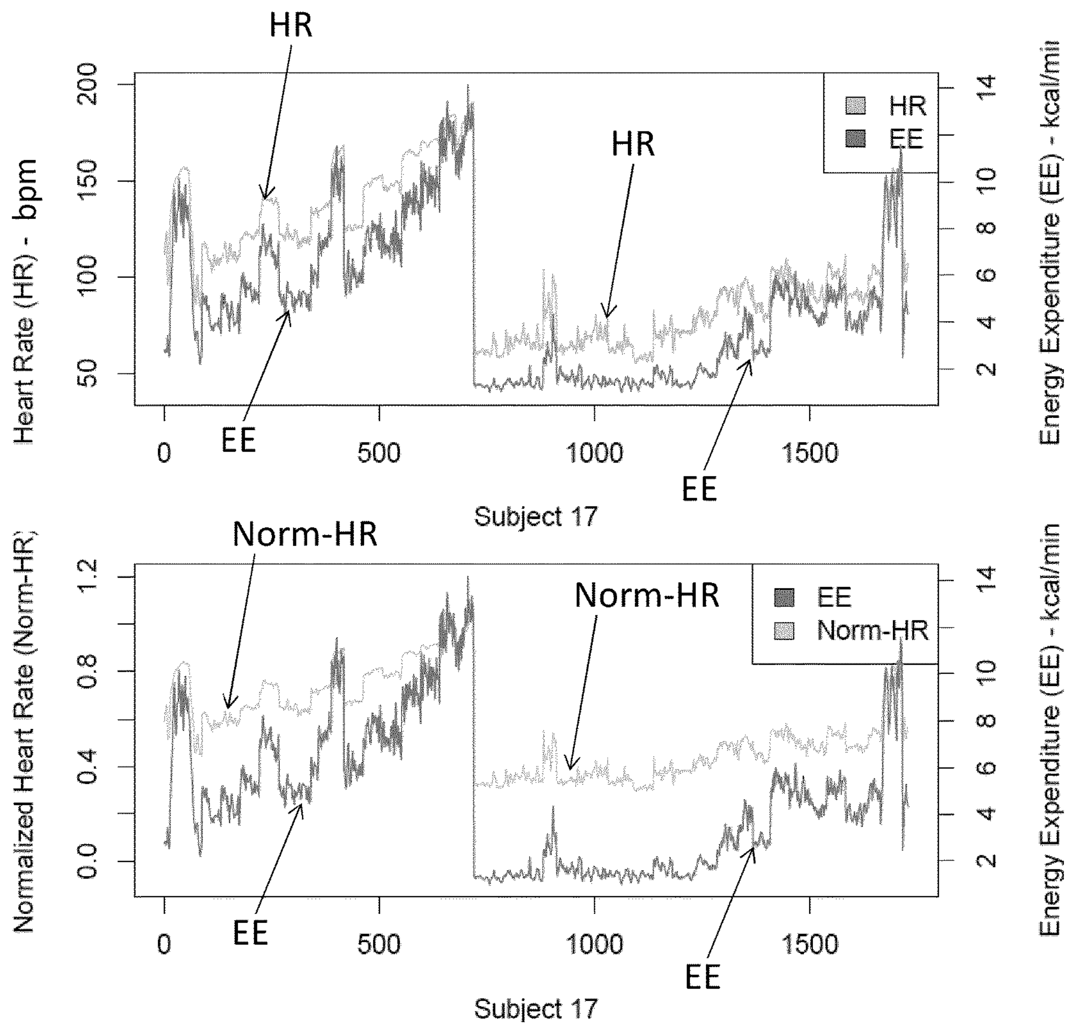
FIGS. 4A and 4B illustrate a relation between heart rate and cardiorespiratory fitness according to one embodiment, and the results obtained when applying the scaling factor to normalize heart rate for a first human subject (FIG. 4A) and a second human subject (FIG. 4B).
Figure 4B:
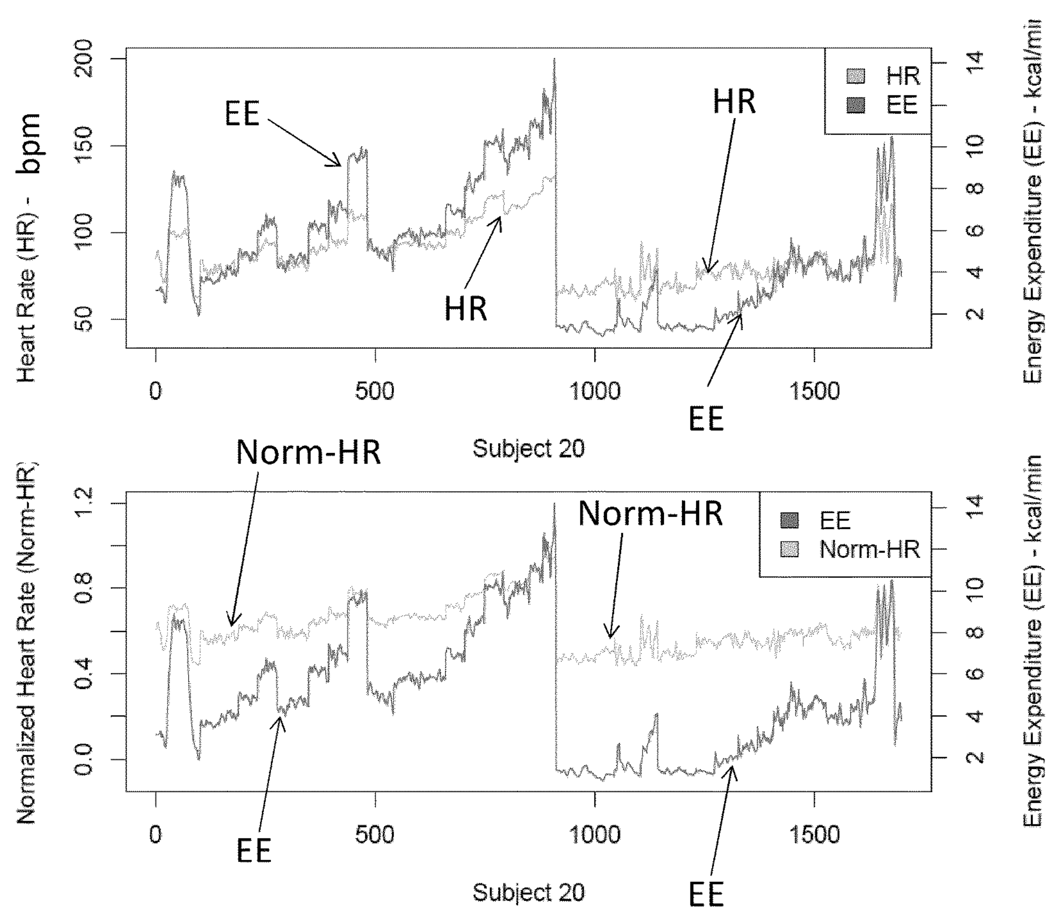

The effect of this normalization, according to an exemplary embodiment, is shown in FIG. 4A and FIG. 4B. In FIG. 4A and FIG. 4B two human beings with similar body weight are compared. Energy expenditure EE during a set of activities is similar, while heart rate HR differs (top row plots). This difference makes it impossible to estimate energy expenditure accurately based on current or real-time heart rate information. After performing heart rate normalization using the scaling factor the normalized heart rate Norm-HR is similar (bottom row plots), since cardiorespiratory fitness is accounted for, and therefore energy expenditure EE can be estimated more accurately. The reduction in Root Mean Square Error (RMSE) can be seen in FIG. 6, for different activities of the subject. RMSE is reduced from 0.60 to 0.58 kcal/min for "dynamic" (3% error reduction, not significant), from 1.13 to 0.81 kcal/min for "walking" (28% error reduction, $p=0.00027<\alpha$), from 1.38 to 0.92 kcal/min for "biking" (33% error reduction, $p=0.00037<\alpha$) and from 1.25 to 0.89 kcal/min for "running" (29% error reduction, $p=0.01<\alpha$).

The functions of the modules described in FIG. 1, according to some embodiments, may be implemented using hardware and/or software components, for example using a microcontroller or digital signal processor or any other multi-purpose integrated circuit comprising instruction processing capability, interface circuitry and memory.

Figure 2:
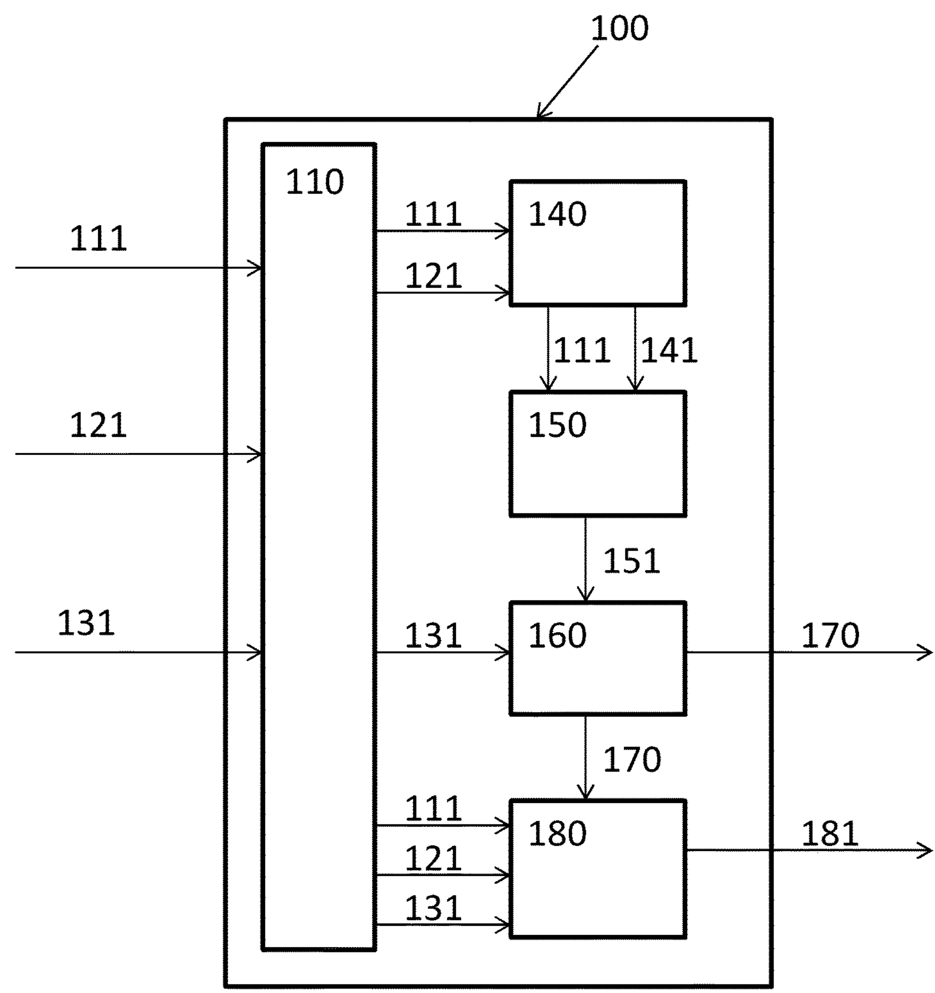
FIG. 2 shows a block diagram of a second embodiment of a device for monitoring the physical activity of a living being.

FIG. 2 shows a second block diagram of one embodiment of a device 100 for monitoring the physical activity of a living being comprising the same elements as the device shown in FIG. 1 plus an energy expenditure module 180 which calculates an energy expenditure 181 of a living being using the living being's cardiorespiratory fitness level 170, detected activity 141, motion intensity 121, heart beat rate values 111 and any of the the anthropometric characteristics 131.

Figure 5:
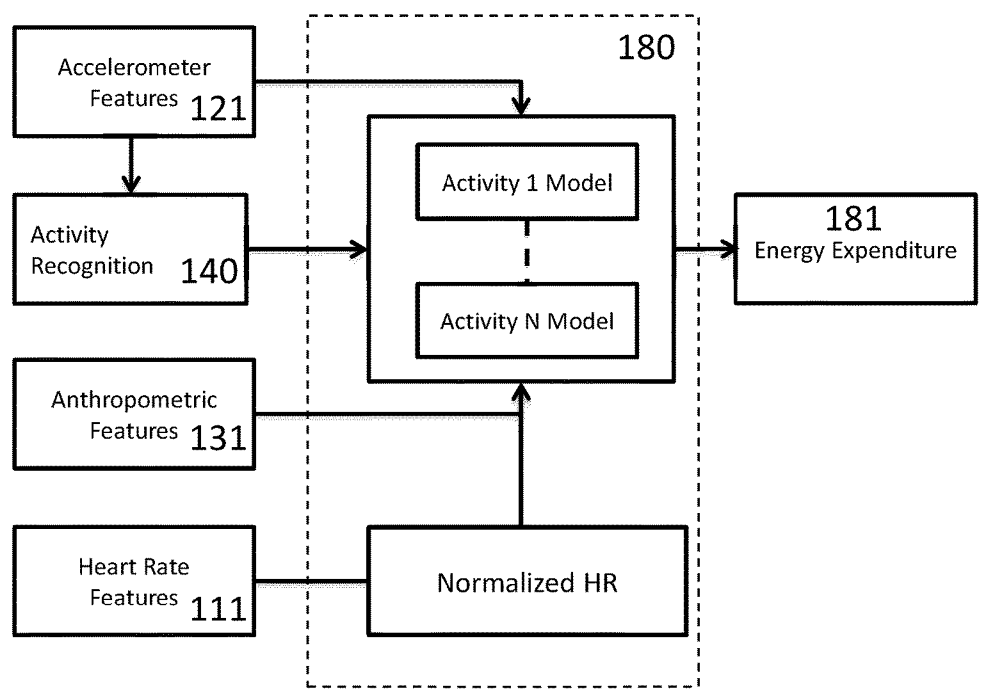
FIG. 5 shows a block diagram of an energy expenditure estimation algorithm together with heart rate feature scaling according to one embodiment.
Figure 6:
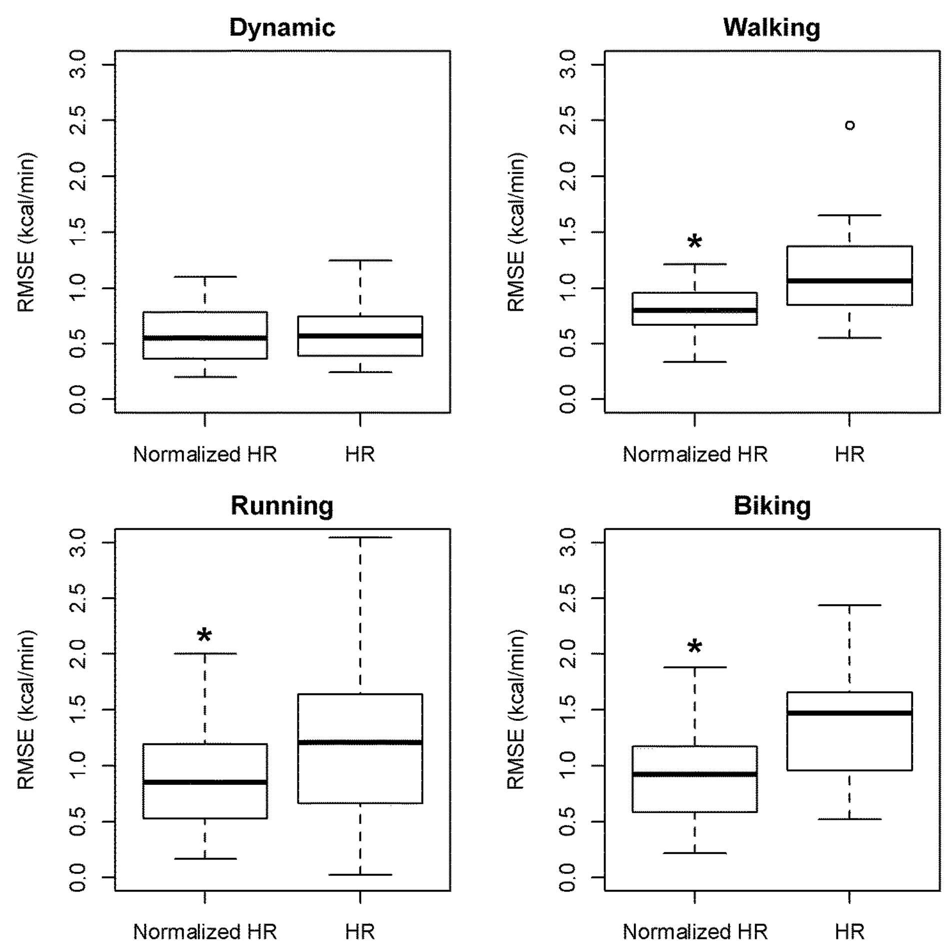
FIG. 6 shows results provided by the energy expenditure algorithms in terms of error reduction when a device according to one embodiment is used.

State of the art energy expenditure estimation algorithms calculate energy expenditure in two steps: first, an activity is recognized by using the activity recognition module; the activity recognition module uses motion information from a motion module (e.g. accelerometer) to derive the activity performed by a human being; and secondly, an activity-specific energy expenditure model is applied to derive energy expenditure. An activity-specific energy expenditure model can be a multiple linear regression model (or a non-linear model) developed using motion information, heart rate information, anthropometric characteristics and reference VO2 from a number of human beings performing the specific activity. A different model is used for each detected activity in order to capture the peculiar relation between an activity and energy expenditure. An example of such procedure is illustrated in FIG. 5. More details on this approach can be found in "*Energy Expenditure Estimation Using Wearable Sensors: A New Methodology for Activity-Specific Models*" by Altini M., Penders J, Amft O. According to one embodiment, energy expenditure can be estimated using the normalized heart rate (or cardiorespiratory fitness level), thus significantly reducing the error by taking into account that heart rate varies largely between individuals, due to differences in cardiorespiratory fitness level, as shown in FIG. 4A and FIG. 4B and FIG. 6.

FIG. 3 illustrates the distribution of a plurality of heart beat rate values associated with four detected activities, used for calculating statistics of the distribution of heart beat values according to one embodiment.

According to one embodiment, the activity recognition and storage module 140 is able to determine both a rest activity and a moving activity of the living being, and stores heart beat rate values 111 associated with each of the detected activities 141, and the motion intensity associated to the moving activity.

According to one embodiment, the moving activity is associated to at least a first motion intensity and a second motion intensity and the heart beat rate analysis module 150 determines one first heart beat rate summary from the heart beat rate value distribution associated to the first motion intensity and one second heart beat rate summary from the heart beat rate value distribution associated to the second motion intensity and one third heart beat rate summary from the heart beat rate value distribution associated to the rest activity. According to one embodiment, a summary of the heart beat rate value distribution can be for example the calculation of the mean of the heart rate value distribution for an activity or subset of activities. FIG. 3A and FIG. 3B show an example of how to derive cardiorespiratory fitness level or the heart rate scaling factor, from, for example, the mean of the heart rate values while at rest and walking at 4, 5 and 6 km/h, together with age and height. The specific heart rate scaling factor can be used to normalize the heart rate of the activity-specific EE models, and predict EE more accurately. It is understood that other different walking speeds could be also used in another embodiments.

Examples of models for calculating the CRF and the HR scaling factor are, for example, multiple linear regression models. The coefficients of the multiple linear regression models can be derived using information about activity performed, heart beat rate distribution, acceleration, anthropometric characteristics and VO2 reference from indirect calorimetry from a number of human beings performing a range of activities. The same could be applied for models related to animal beings.

What is claimed is:

1. A device for calculating an energy expenditure of a particular living being, the device comprising:

a data input module configured to receive information about the living being's heart beat rate values, motion intensity, and anthropometric characteristics;

an activity recognition and storage module configured to recognize, from information received about the living being's motion intensity, a rest activity and at least two motion activities of the particular living being, the activity recognition and storage module further configured to store the living being's heart beat rate values during the recognized rest activity and the at least two recognized motion activities, the activity and recognition and storage module further configured to store data of the particular living being's acceleration sensed during the at least two recognized motion activities;

a heart beat rate analysis module configured to determine, from a plurality of the heart beat rate values stored during the recognized rest activity and the at least two recognized motion activities, a mean or median of the distribution of the heart beat rate values stored during the recognized rest activity and the at least two recognized motion activities of the particular living being;

a fitness estimation module configured to calculate, using the mean or median of the distribution of heart beat rate values stored during the recognized rest activity and the at least two recognized motion activities performed by the living being and the anthropometric characteristics, a cardiorespiratory fitness level of the particular living being; and an energy expenditure module configured to calculate a heart rate scaling factor value using a multiple linear regression model that expresses the relation between the anthropometric characteristics of the particular living being, the acceleration data stored during the at least two recognized motion activities of the particular living being, and the mean or median of the distribution of the heart beat rate values stored during the recognized rest activity and the at least two recognized motion activities of the particular living being, the energy expenditure module further configured to calculate normalized heart beat rate values by dividing the particular living being's heart beat rate values stored during the particular living being's recognized rest activity and the at least two recognized motion activities by the calculated heart rate scaling factor value, the energy expenditure module further configured to calculate the energy expenditure of the particular living being using a mathematical model that expresses the relation between the cardiorespiratory fitness level calculated by the fitness estimation module, the recognized rest activity and the at least two recognized motion activities of the particular living being, the acceleration data stored during the at least two recognized motion activities of the particular living being, the calculated normalized heart beat rate values, and the anthropometric characteristics of the particular living being, at least one of the modules using a processor configured to execute software.

2. The device according to claim 1, wherein the information about motion intensity is information about the body's acceleration or motion speed.

3. The device according to claim 1, wherein the information about motion intensity is information about the body's acceleration and the device further comprises a motion calculation component configured to calculate, from the information about the body's acceleration, the living being's motion speed.

4. The device according to claim 1, wherein the information about motion intensity is information about the body's acceleration and the device further comprises a location positioning component configured to calculate the living being's motion speed.

5. The device according to claim 1, wherein the at least two recognized motion activities comprise walking at a first pace and walking at a second, different pace, and the heart beat rate analysis module is configured to calculate the mean or median of the distribution of the heart beat rate values stored during the recognized walking at the first pace and walking at the second, different pace.

6. The device according to claim 1, wherein the fitness estimation module uses a mathematical model based on the mean or median of the distribution of heart beat rate values stored during the recognized rest activity and the at least two recognized motion activities of the particular living being, the acceleration data stored during the at least two recognized motion activities of the particular living being, the anthropometric characteristics, and VO2 reference from indirect calorimetry.

7. The device according to claim 1, wherein a first motion intensity is associated to a first motion activity of the at least two recognized motion activities and a second motion intensity is associated to a second motion activity of the least two recognized motion activities, and wherein the heart beat rate analysis module is configured to determine the mean or median of the distribution of heart beat rate values stored during the first motion intensity and the mean or median of the distribution of heart beat rate values stored during the second motion intensity and the mean or median of the distribution of heart beat rate values stored during the recognized rest activity.

8. The device according to claim 1, wherein the living being is a human or an animal being.

9. The device according to claim 8, wherein the living being is a human and the anthropometric characteristics comprise one or more of a gender, BMI, height, age, and weight characteristic.

10. The device according to claim 1, configured to receive information from sensors directly connected to the device or further comprising a wireless transmission module which receives information from sensors located in the living being.

11. A method of calculating an energy expenditure of a particular living being, the method comprising:

inputting information about the living being's anthropometric characteristics into an input user interface and sensing information about the living being's motion intensity;

receiving, from an electronic heart beat rate sensor, information about the living being's heart beat rate values;

recognizing, from information received about the living being's motion intensity, a rest activity and at least two motion activities of the particular living being;

storing the living being's heart beat rate values during the recognized rest activity and the at least two recognized motion activities, and storing data of the particular living being's acceleration sensed during the at least two recognized motion activities;

determining, from a plurality of the heart beat rate values stored during the recognized rest activity and the at least two recognized motion activities, a mean or median of the distribution of the heart beat rate values stored during the recognized rest activity and the at least two recognized motion activities of the particular living being;

calculating, in a processor, a cardiorespiratory fitness level of the particular living being using the mean or median of the distribution of heart beat rate values stored during the recognized rest activity and the at least two recognized motion activities performed by the particular living being and the anthropometric characteristics;

calculating, in the processor, a heart rate scaling factor value using a multiple linear regression model that expresses the relation between the anthropometric characteristics of the particular living being, the acceleration data stored during the at least two recognized motion activities of the particular living being, and the mean or median of the distribution of the heart beat rate values stored during the recognized rest activity and the at least two recognized motion activities of the particular living being;

calculating, in the processor, normalized heart beat rate values by dividing the particular living being's heart beat rate values stored during the particular living being's recognized rest activity and the at least two recognized motion activities by the calculated heart rate scaling factor value; and calculating, in the processor, the energy expenditure of the particular living being using a mathematical model that expresses the relation between the cardiorespiratory fitness level calculated by the fitness estimation module, the recognized rest activity and the at least two recognized motion activities of the particular living being, the acceleration data stored during the at least two recognized motion activities, the anthropometric characteristics of the particular living being, and from the calculated normalized heart beat rate values.

12. A device for calculating an energy expenditure of a particular living being, the device comprising:

means for receiving information about the living being's heart beat rate values, motion intensity, and anthropometric characteristics;

means for recognizing a rest activity and at least two motion activities of the particular living being from information received about the living being's motion intensity, the means for recognizing comprising means for storing the living being's heart beat rate values during the recognized rest activity and the at least two recognized motion activities, the means for recognizing further comprising means for storing data of the particular living being's acceleration sensed during the at least two recognized motion activities;

means for determining, from a plurality of the heart beat rate values stored during the recognized rest activity and the at least two recognized motion activities, a mean or median of the distribution of the heart beat rate values stored during the recognized rest activity and the at least two recognized motion activities of the particular living being;

means for calculating, using the mean or median of the distribution of heart beat rate values stored during the recognized rest activity and the at least two recognized motion activities performed by the living being and the anthropometric characteristics, a cardiorespiratory fitness level of the particular living being;

means for calculating a heart rate scaling factor value using a multiple linear regression model that expresses the relation between the anthropometric characteristics of the particular living being, the acceleration data stored during the at least two recognized motion activities of the particular living being, and the mean or median of the distribution of the heart beat rate values stored during the recognized rest activity and the at least two recognized motion activities of the particular living being;

means for calculating normalized heart beat rate values by dividing the particular living being's heart beat rate values stored during the particular living being's recognized rest activity and the at least two recognized motion activities by the calculated heart rate scaling factor value; and means for calculating the energy expenditure of the particular living being using a mathematical model that expresses the relation between the cardiorespiratory fitness level calculated by the fitness estimation module, the recognized rest activity and the at least two recognized motion activities of the particular living being, the acceleration data stored during the at least two recognized motion activities of the particular living being, the calculated normalized heart beat rate values, and the anthropometric characteristics of the particular living being, at least one of the means for receiving, the means for recognizing, the means for determining, the means for calculating a cardiorespiratory fitness level, and the means for calculating the energy expenditure using a processor configured to execute software.

13. The device according to claim 1, wherein the data input module is configured to receive information about the living being's heart beat rate value from a heart beat rate sensor or an ECG sensor.

14. The device according to claim 1, wherein the data input module is configured to receive information about the living being's motion intensity from an accelerometer sensor or a GPS device.

15. The method according to claim 1, wherein the cardiorespiratory fitness level of the particular living being is continuously and automatically recalculated in the processor over a time.

* * * * *